Figure 1:
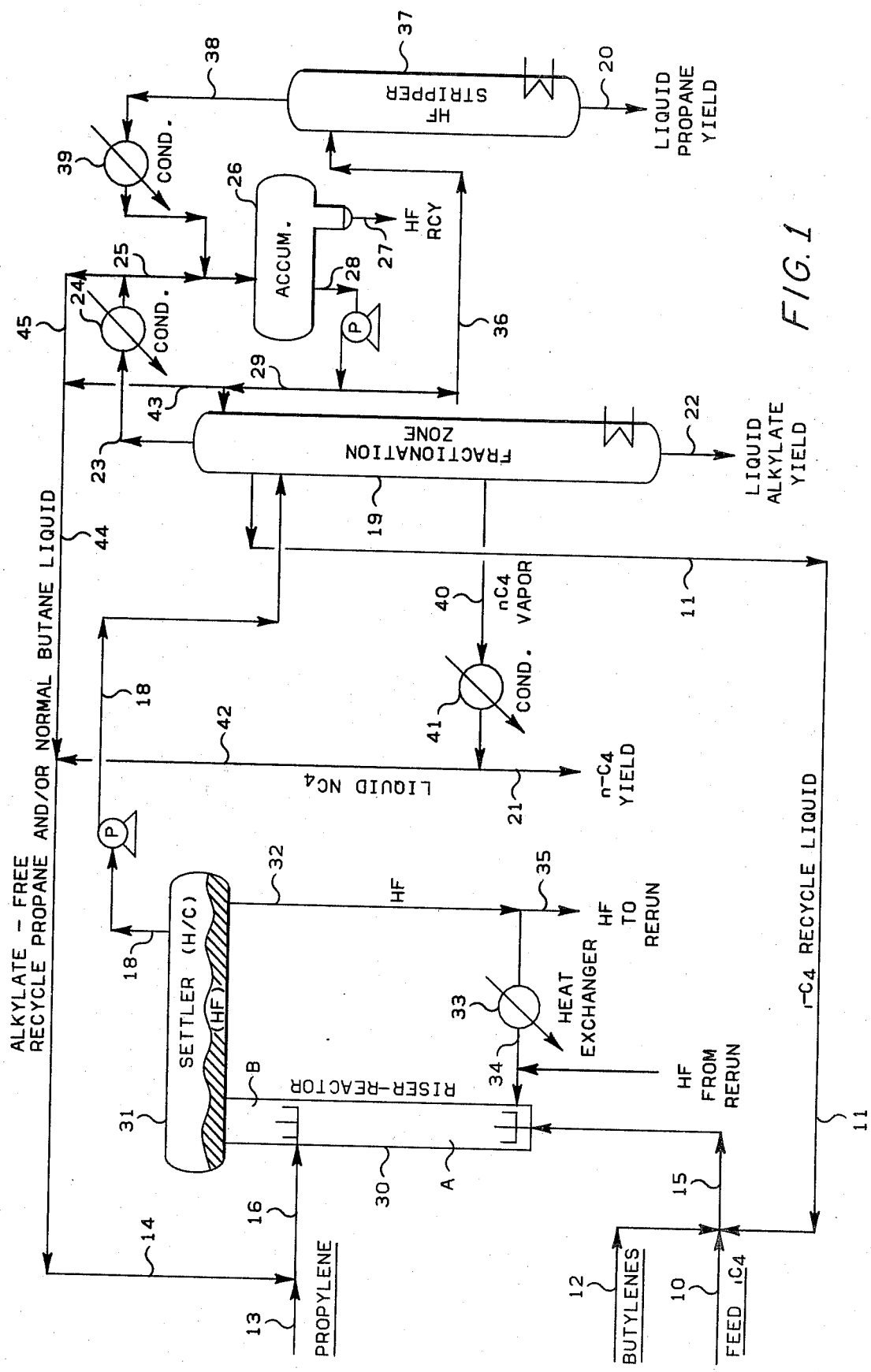

United States Patent [19]

Hutson, Jr.

[11] 4,225,742
[45] Sep. 30, 1980

[54] ALKYLATION PROCESS

[75] Inventor: Thomas Hutson, Jr., Bartlesville, Okla.

[73] Assignee: Phillips Petroleum Company, Bartlesville, Okla.

[21] Appl. No.: 924,332

[22] Filed: Jul. 13, 1978

Related U.S. Application Data

[63] Continuation-in-part of Ser. No. 839,728, Oct. 5, 1977, abandoned.

[51] Int. Cl.$^2$ ............................................. C07C 3/54
[52] U.S. Cl. ................................................. 585/723
[58] Field of Search .................... 260/683.48; 585/723

[56] References Cited

U.S. PATENT DOCUMENTS

| | | | |
|---|---|---|---|
| 2,399,368 | 4/1946 | Matuszak | 260/683.48 |
| 2,910,521 | 10/1959 | Cobb | 260/683.48 |
| 3,080,438 | 3/1963 | Sailors | 260/683.48 |
| 3,169,152 | 2/1965 | VanPool et al. | 260/683.48 |
| 3,169,153 | 2/1965 | Walker et al. | 260/683.48 |
| 3,233,007 | 2/1966 | Chapman | 260/683.48 |
| 3,246,047 | 4/1966 | Chapman et al. | 260/683.48 |
| 3,249,649 | 5/1966 | Sherk et al. | 260/683.48 |
| 3,272,888 | 9/1966 | Logan et al. | 260/683.43 |
| 3,281,213 | 10/1966 | Waddill | 23/285 |
| 3,365,514 | 1/1968 | Slover | 260/683.48 |
| 3,716,343 | 2/1973 | Chapman | 23/285 |
| 3,806,588 | 4/1974 | Hann | 423/484 |
| 3,998,903 | 12/1976 | Sobel | 260/683.48 |

*Primary Examiner*—C. Davis

[57] ABSTRACT

In the HF alkylation of isoparaffins with olefins an improved process is provided comprising charging isoparaffin, olefin(s), and HF catalyst to the upstream end of a vertically extended reaction zone, introducing the same or different olefin(s) and, optionally, isoparaffin, downstream along with a recycled alkane stream separated from the alkylation effluent under alkylation conditions to produce high octane alkylate. In a preferred embodiment, the recycle alkane stream is propane and/or normal butane.

15 Claims, 2 Drawing Figures

ALKYLATION PROCESS

This application is a continuation-in-part application of pending application having Ser. No. 839,728, filed Oct. 5, 1977, and now abandoned.

This invention relates to an improved process for alkylation. In accordance with another aspect, this invention relates to an improved process for alkylating isoparaffin with a plurality of olefins and the introduction of recycle alkane hydrocarbon separated from the alkylation effluent into the reaction zone at the downstream points of olefin injection. In accordance with another aspect, this invention relates to an improved alkylation process having series HF and isoparaffin flow together with parallel injection of the same or different olefin(s) at spaced loci along a vertically extended reaction zone and the introduction of recycle alkane hydrocarbons at the downstream points of olefin(s) injection. In accordance with a further aspect, this invention relates to an improved HF alkylation process comprising series HF and isoparaffin flow, parallel injection of at least two different olefins at spaced points along a vertically extended reaction zone, with recycle of at least one alkane separated from the hydrocarbon effluent to each point of downstream olefin injection into the reaction zone. In accordance with a further aspect, all of the isoparaffin, e.g., isobutane (feed and recycle), is added to the upstream locus and the diluent alkane, e.g., propane and/or normal butane, is added to the downstream points of addition of olefin(s) and the olefin or olefins added at all points are the same.

The alkylation of an isoparaffin such as isobutane or isopentane with olefins such as propylene, butylens, and amylenes has been practiced utilizing various alkylation cataysts, particularly HF acid. In applications where more than one olefin is to be reacted with an isoparaffin, it is customary to either inject both olefins into a reactor, along with isoparaffin, or to conduct two separate alkylation steps in different reactors. Some prefer alkylating in separate reactors with different olefins because a higher yield and higher quality alkylate can be produced in each instance. This is due to the fact that optimum reaction conditions are different for different light olefins such as propylene, butylenes, and amylenes. This invention is concerned with a method and apparatus for alkylating an isoparaffin with two or more light olefins in a single reactor which results in a high yield of high quality alkylate. The present invention relates to an improved alkylation having parallel injection of a plurality of olefins for increasing the alkylate octane number by recycling an alkane portion fractionated from the alkylation hydrocarbon effluent at each downstream olefin injection to obtain desirable olefin dilution plus maintaining a high isoparaffin to olefin ratio along the length of a vertically extended reaction zone.

Accordingly, an object of this invention is to provide an improved process for alkylating an isoparaffin with a plurality of olefins in a single reaction zone.

A further object of this invention is to provide a process of alkylation in which a downstream portion of an elongated reaction zone is diluted with alkanes fractionated from the effluent.

Another object of this invention is to provide a process which produces an improved yield of high quality alkylate.

Other objects, aspects, and the several advantages of this invention will be apparent to those skilled in the art upon a study of this disclosure, the drawings, and the appended claims.

According to the invention set forth in said copending application, an improved HF alkylation process is provided comprising plural spaced introduction of different olefins along a vertically extended reaction zone plus dilution of olefins introduced downstream with a recycle alkane stream to produce high octane alkylate.

In accordance with the present invention, an improved HF alkylation process is provided comprising plural spaced introduction of the same olefin or olefins along a vertically extended reaction zone plus dilution of olefins introduced at all points of olefin introduction but preferably at the downstream point with a recycle alkane stream such as propane and/or normal butane to produce high octane alkylate. In addition, it is within the scope of this embodiment of the invention to introduce feed or makeup isoparaffin, e.g., isobutane, at the stream or inlet and locus of olefin introduction or in part as feed isoparaffin to all points of olefin introduction.

In a preferred embodiment of multiple-based introduction of the same olefin(s), all of the isoparaffin, e.g., isobutane (feed and recycle), is added to the upstream locus and the diluent recycle alkane, e.g., propane and/or normal butane, is added to the downstream locus and the olefin or olefins being the same composition are added to all points of introduction of olefin.

Thus, in accordance with a specific embodiment, an improved HF alkylation process is provided comprising series HF and isoparaffin flow, parallel injection of the same or different olefin(s) at spaced points or loci along a vertically extended alkylation reaction zone, and recycle of an alkane stream substantially free of alkylate separated from the hydrocarbon effluent obtained from the alkylation process.

In another embodiment, heavier olefin is introduced into a vertically extended reaction zone at the inlet end and at least one different lighter olefin is introduced at an intermediate locus or loci along the vertically extended alkylation zone, and a recycle alkane stream comprising propane and/or normal butane substantially free of alkylate is recycled to each point of downstream olefin injection.

In one specific embodiment, butylene is introduced at the inlet end of the alkylation zone and propylene is introduced into the reaction zone at an intermediate point, and propane and/or normal butane separated from the alkylation effluent are recycled and introduced along with propylene or introduced separately into the reaction zone at an intermediate point.

In another specific embodiment, the lighter olefin is introduced into a vertically extended reaction zone at the inlet end and the introduction of at least one different heavier olefin at an intermediate locus or loci along the vertically extended alkylation zone, and a recycle alkane stream comprising propane and/or normal butane substantially free of alkylate is recycled to each point of downstream olefin injection.

In one particular embodiment, propylene is introduced at the inlet end of the alkylation zone and a butylene is introduced into the reaction zone at one or more intermediate points, and propane and/or normal butane separated from the alkylation effluent are recycled and introduced along with the butylene or introduced separately into the reaction zone at each intermediate point.

In general, any of the conventional catalytic alkylation reactions can be carried out by the method of the present invention. Thus, the alkylation reaction can comprise reaction of an isoparaffin with an olefin or other olefin-acting alkylatable material carried out in the presence of a suitable alkylation catalyst. Suitable olefins include propylene, butenes, pentenes, hexenes, and the like, as well as mixtures thereof. An admixture of propylene and butylenes is often used, particularly when the same olefin or olefins are charged to spaced points along the reaction zone. Suitable isoparaffins include isobutane, isopentane, and the like. A wide variety of alkylation catalysts can be employed in the alkylation reaction, but HF acid is presently preferred.

The alkylation reaction can be carried out under a wide range of conditions, but ordinarily sufficient pressure is used to maintain liquid phase conditions and a temperature sufficient to form alkylate. In the present invention, when butylene(s) are charged to the inlet end, the temperature at the inlet end of the vertically extended reaction zone ranges from about 50° F. to about 100° F., a pressure of about 120 to about 200 psig, a total isoparaffin/olefin mole ratio of about 7.5 to 1 to about 40 to 1, an HF to total hydrocarbon volume ratio of about 1 to 1 to about 10 to 1, and a residence time in the range of about 20 to about 200 seconds.

The conditions in the alkylation zone downstream from the inlet and in proximity of the points of injection of different olefins will vary from those at the inlet end. In this embodiment, when propylene is added at the downstream locus, the temperature will range from about 80° F. to about 125° F. and sufficient pressure to maintain liquid phase conditions, e.g., about 120 to about 200 psig. The total paraffin (recycle paraffin plus isoparaffin) to olefin volume ratio will range from about 7 to 1 to about 36 to 1, the HF to total hydrocarbon volume ratio will range from about 1 to 1 to about 10 to 1, and the residence time will range from about 25 to about 200 seconds. The amount of hydrocarbon separated from the alkylation effluent and recycled to the intermediate loci of the alkylation reaction zone is sufficient to provide a hydrocarbon to different olefin volume ratio of about 2 to 1 to about 50 to 1.

When propylene is charged the inlet end of the reaction zone and a butylene is charged to an intermediate locus or loci of the reaction zone, the temperature at the inlet will be in the range of about 80° F. to about 120° F. and sufficient pressure to maintain liquid phase conditions, e.g., about 120 to about 200 psig. The total paraffin (recycle paraffin plus isoparaffin) to olefin volume ratio will be in the range of about 7 to 1 to about 40 to 1, the HF to total hydrocarbon volume ratio will be in the range of about 1 to 1 to about 10 to 1, and a residence time in the range of about 20 to about 200 seconds.

The conditions in the alkylation zone downstream from the inlet end in proximity of the points of injection of different olefins will vary from those at the inlet end when a butylene is added at the downstream locus in that the temperature will be in the range of about 50° F. to 100° F., a pressure of about 120 to about 200 psig, to maintain liquid phases, a total paraffin (recycle paraffin plus isoparaffin) to olefin volume ratio in the range of about 7 to 1 to about 36 to 1, the HF to total hydrocarbon volume ratio of about 1 to 1 to about 10 to 1, and the residence time will be in the range of about 20 to about 200 seconds. The amount of hydrocarbon separated from the alkylation effluent to the intermediate loci of the alkylation reaction zone is sufficient to provide a hydrocarbon to different olefin ratio of about 2 to 1 to about 50 to 1.

The conditions in the alkylation zone downstream from the inlet end in proximity of the points of injection of the same olefin or different olefins can vary from those at the inlet end but ordinarily will be approximately the same. In this embodiment, when propylene or butylene or a mixture of propylene and butylene is added at the inlet end, the temperature will range from about 50° F. to about 120° F. and sufficient pressure to maintain liquid phase conditions, e.g., about 120 to about 200 psig. When the olefin is propylene, temperature will range from about 100° F. to about 125° F.; for butenes, about 50° F. to about 100° F., and for mixtures of propane and butylenes, about 50° F. to 100° F. (usually major portion is butylenes in mixtures). The conditions of temperature at the downstream locus or loci will range from about 50 to about 120° F. with the pressure still being sufficient to maintain liquid phase conditions. The same ranges of temperature are used as at the inlet end when the same olefin or mixture is charged to the inlet and the downstream loci. The total paraffin (recycle paraffin plus isoparaffin) to olefin volume ratio will range from about 7 to 1 to about 40 to 1, the HF to total hydrocarbon volume ratio will range from about 1 to 1 to about 10 to 1, and the residence time will range from about 20 to about 200 seconds. The amount of hydrocarbon separated from the alkylation effluent and recycled to the intermediate loci, as well as the inlet locus of the alkylation reaction zone, is sufficient to provide a hydrocarbon to olefin volume ratio of about 2 to 1 to about 50 to 1.

The alkane hydrocarbons separated and recycled from the alkylation effluent comprises principally normal $C_3$ and $C_4$ paraffin hydrocarbons freed of alkylate by fractionation and a sufficient amount of hydrocarbon is separated and recycled to each downstream olefin injection to provide the amount of recycle hydrocarbon set forth above. If desired, the diluent alkane recycle, e.g., propane and/or normal butane, can also be introduced at the inlet end of the alkylation zone. The temperature of the recycle hydrocarbon can be adjusted prior to injection into the alkylation reaction zone so as to provide temperature control of the reaction at each olefin injection diluted with recycle alkane. The recycle alkane hydrocarbon can enter with the olefin or separately can be introduced into the alkylation reaction zone. It is presently preferred to recycle propane and/or n-butane separated from the alkylation effluent, and is used in an amount of about 3 to about 20 volume percent of the recycle isobutane.

Figure 2:
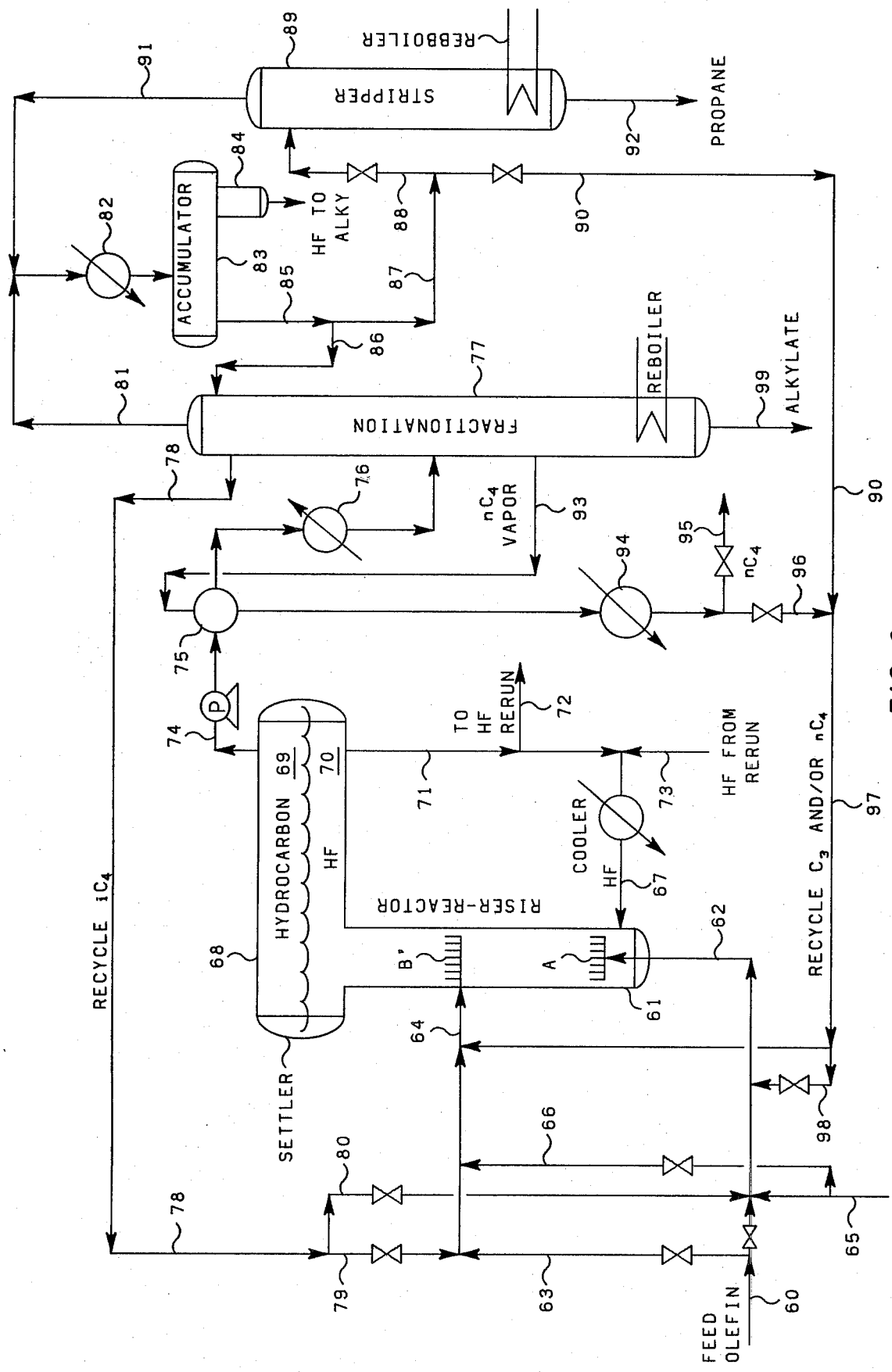

A better understanding of the invention will be had upon reference to the accompanying schematic drawings in which FIG. 1 embodies one arrangement of apparatus for effecting the invention wherein different olefins are introduced at different locations into the alkylation zone and FIG. 2 embodies another arrangement of apparatus for effecting the invention wherein the same olefin or olefins are introduced at all points of olefin introduction.

Referring to FIG. 1, a tubular riser-reactor 30 is connected at the outlet end with acid settler 31 which is provided with a take-off line 18 for the hydrocarbon alkylate-containing phase being removed from the settler. An acid return line 32 connects with the bottom section of settler 31 and can be passed through acid cooler 33 and then line 34 for introduction into the inlet end of riser-reactor 30. Some of the recycle HF acid can be withdrawn through line 35 and passed to a rerun unit (not shown) and returned to the process.

Feed isobutane in line 10 is mixed with butylene introduced by line 12 and recycle isobutane by line 11, and the combined stream is passed by way of line 15 and introduced into the inlet end of riser-reactor 30. In the drawing the inlet end portion of riser-reactor 30 is identified as Zone A and the downstream end of the reactor is labelled Zone B. The alkylation feed introduced by way of line 15 into riser-reactor 30 is contacted with HF acid at the inlet end and subjected to alkylation conditions such that alkylate is formed and is passed through riser-reactor 30 to the outlet end and introduced into a lower protion of settler 31.

Propylene in line 13 is combined with alkylate-free recycle propane and/or normal butane in line 14 and the resulting mixture is introduced by way of line 16 into an intermediate portion of riser-reactor 30 also identified as Zone B. The propylene introduced into reaction mixture is subjected to conditions such that additional alkylate is formed and is passed along with previously formed alkylate into a lower portion of settler 31.

The alkylation rection effluent introduced into settler 31 is allowed to phase separate into an upper hyrocarbon phase and a lower HF acid phase. The upper hydrocarbon phase is removed from settler 31 by way of line 18 and passed to fractionation zone 19 wherein the hydrocarbon effluent is subjected to such fractionation conditions as to take overhead by line 23 propane and lighter materials which are cooled in cooler 24, and the cooled condensate is passed at least in part by way of line 25 to accumulator 26. HF is withdrawn from a lower portion of accumulator 26 by way of line 27. Hydrocarbon condensate is withdrawn from accumulator 26 by line 28 and returned in part by way of line 29 as reflux to an upper portion of fractionation zone 19. The remainder of the hydrocarbon condensate removed from accumulator 26 is passed by way of line 36 to HF stripper 37 wherein the stream is subjected to conditions such that HF and propane are taken overhead by way of line 38 and cooled in cooler 39 and returned to accumulator 26. The liquid propylene yield is removed from the lower portion of stripper 37 by way of line 20.

Isobutane separated in fractionation zone 19 is removed by way of line 11 and recycled to the inlet end of riser-reactor 30, combining with feed isobutane and butylene in contact with HF acid catalyst.

Normal butane vapor is withdrawn from the fractionation zone 19 by way of line 40 and passed through cooler 41 wherein it is cooled sufficiently to form liquid butane. A portion of the liquid butane is passed by way of line 42 and line 44 for dilution of propylene introduced into an intermediate portion of riser-reactor 30. The remainder of the liquid normal butane is yielded as product by way of line 21 for further use as desired.

It is also within the scope of the invention to pass a portion of the propane condensate removed from accumulator 26 and pass same through line 43 and combine with line 44 and line 14 for dilution of propylene introduced into an intermediate portion of riser-reactor 30. If desired, a portion of the condensate removed overhead from fractionation zone 19 can be passed by way of line 45, line 44, and line 14 for dilution of propylene feed to the alkylation zone. Product alkylate is recovered via line 22.

Referring now to FIG. 2, feed olefin in line 60 comprising propylene or butylene or a mixture of propylene and butylene is introduced into the inlet end of riser-reactor 61 by way of line 62 at the inlet end of riser-reactor 61 and by way of lines 63 and 64 to an intermediate point downstream of riser-reactor 61. Feed isobutane in line 65 is combined with feed olefin in line 62 and introduced into the inlet end of riser-reactor 61. If desired, feed isobutane can also be passed by way of valved line 66 for introduction into the downstream point in the reactor by way of line 64. HF acid catalyst is introduced into the inlet end of riser-reactor 61 by way of line 67 and mixed with feed isobutane and feed olefin under alkylation conditions sufficient to produce alkylate.

The alkylation zone 61 effluent is passed to settling zone 68 wherein the effluent is allowed to separate into an upper hydrocarbon phase 69 and a lower HF acid phase 70. The acid phase 70 is withdrawn from settler 68 by way of line 71 and a part sent to an HF rerun unit (not shown) by way of line 72 and the remainder returned after cooling by way of line 67 to reactor 61. HF from rerun unit (not shown) is introduced into the system by way of line 73.

Hydrocarbon phase 69 is withdrawn from settler 68 by way of line 74 and pumped through heat exchangers 75 and 76 before being introduced into fractionation zone 77. The hydrocarbon phase removed from settler 68 comprises alkylate product, unreacted isoparaffin, e.g., isobutane, propane, normal butane, and trace amounts of HF acid. Within fractionation zone 77 hydrocarbon phase feed is subjected to fractionation conditions such that isobutane is withdrawn from an upper portion thereof by way of line 78 and recycled to the alkylation zone. The recycle isobutane can be introduced by line 64 by way of valved line 79 or into line 62 by way of valved line 80.

An overhead stream comprising propane, and some HF is removed from fractionation zone 77 by way of line 81, passed through cooler 82 to condense the condensible materials, and the cooled overhead is passed to accumulator 83. HF acid is removed from a lower portion of accumulator 83 by way of withdrawal keg 84 and returned to the alkylation zone for reuse as desired. The hydrocarbon condensate is removed from accumulator 83 by way of line 85 and part of the condensate is passed as reflux to an upper portion of fractionation zone 77 by way of line 86. The remainder is passed by way of line 87 as feed through valved line 88 to HF stripper 89. A portion of the propane in line 87 can be passed for recycle to the alkylation zone by way of line 90.

In stripper 89 the propane feed containing HF is subjected to stripping conditions such that HF along with some propane is taken overhead by way of line 91 and combined with overhead 81 removed from fractionation zone 77. Propane product or yield is removed as bottoms from stripper 89 by way of line 92.

Normal butane vapor stream is removed from an intermediate portion of fractionation zone 77 by way of line 93 and is passed in heat exchange relationship with the feed in line 74 in heat exchanger 75 and then cooled further in heat exchanger 94. A yield portion of the butane can be withdrawn from the system by way of line 95 and the remainder passed by way of valved line 96 and alone or in combination with propane in line 90 for recycle to the alkylation reactor 61. A mixed stream of propane and normal butane or a stream of either propane or normal butane is passed by way of line 97 for introduction along with olefin in line 64 into an intermediate point of riser-reactor 61. If desired, a portion of this recycled diluent stream can be introduced into line 62 by way of valved line 98.

Product alkylate is withdrawn from a lower portion of fractionation zone 77 by way of line 99.

EXAMPLE I

An alkylation operation based on a calculated example was carried out in an apparatus similar to that shown in FIG. 1 in accordance with the conditions described below.

In the inlet portion of the riser-reactor 30, which is identified as Zone A, the following conditions are used:

| Calculated Example for FIG. 1 Reaction Zone A: | |
|---|---|
| Reactor pressure, psig | 160 |
| Temperature, °F. | 80 |
| $iC_4/C_4$ = mole ratio | 26 |
| HF/HC volume ratio | 4.5/1 |
| Residence time, seconds | 65 |

The conditions obtaining in Zone B, which is downstream from the points of injection of propylene in riser-reactor 30, are as follows:

| Reaction Zone B: | |
|---|---|
| Temperature, °F. | 110 |
| $nC_4/C_3$ = volume ratio | 2/1 |
| $(iC_4 + nC_4)/C_3$ = volume ratio | 24 |
| HF/HC volume ratio | 3.5/1 |
| Residence time, seconds | 65 |

The alkylation operation results in the following flow pattern:

| Stream | Barrels/Day |
|---|---|
| (10) Total $iC_4$ fresh feed | 3,250 |
| (11) Total $iC_4$ recycle | 35,326 |
| (12) Butylenes | 1,250 |
| (13) Propylene | 1,250 |
| (14) Recycle normal butane | 2,500 |
| (20) Propane yield | 500 |
| (21) Normal butane yield | 342 |
| (22) Alkylate yield | 4,450 |
| RON (Clear), estimated | 95-96 |

FIG. 1 and the example show butylenes injected at the lower end of the reactor and propylene at an intermediate locus. Of course, propylene could be added at the lower zone and butylenes intermediate. Normal butane is shown as the diluent for the second (propylene) olefin. Of course, propane alone or propane plus normal butane could be used also as the diluent.

EXAMPLE II

| Calculated Example for FIG. 2 Reaction Zone A': | |
|---|---|
| Reactor pressure, psig | 160 |
| Temperature, °F. | 80 |
| $iC_4/C_4$ = mol ratio | 26 |
| HF/HC volume ratio | 4.5/1 |
| Residence time, seconds | 65 |

-continued

| Calculated Example for FIG. 2 Reaction Zone B': | |
|---|---|
| Reactor pressure, psig | 158 |
| Temperature, °F. | 80 |
| $nC_4/C_4$ = volume ratio | 2/1 |
| $(iC_4 + nC_4)/C_4$ = mol ratio | 26.8 |
| HF/HC volume ratio | 3.5/1 |
| Residence time, seconds | 65 |

| Stream | Barrels/Days |
|---|---|
| (60) Mixed butenes | 2,500 |
| (63) Mixed butenes | 1,250 |
| (62) Mixed butenes (via 62) | 1,250 |
| (65) Feed isobutane (to lower Zone A') | 2,875 |
| (80) Recycle isobutane | 35,326 |
| (97) Recycle normal butane (to Zone B') | 2,500 |
| (92) Propane yield | 250 |
| (95) Normal butane yield | 680 |
| (99) Alkylate yield | 4,500 |
| RON (Clear), estimated | 96-97 |

I claim:

1. A process for alkylating an isoparaffin in the presence of HF acid in a vertically extended reaction zone comprising:
    (a) introducing a liquid mixture comprising an isoparaffin, an olefin, and HF acid catalyst into a lower end portion of said zone,
    (b) introducing at least one olefin into said zone at at least one point substantially downstream of the place of introduction of olefin in (a),
    (c) maintaining suitable conditions of temperature, pressure, and residence time in said reaction zone to form alkylate,
    (d) passing the reaction effluent containing alkylate from said zone to a settling zone to separate an HF acid phase and a hydrocarbon phase containing alkylate and unreacted isoparaffin, HF acid, and normal paraffins,
    (e) fractionating said hydrocarbon phase into a normal paraffin fraction comprising principally normal $C_3$ and $C_4$ paraffin hydrocarbons freed of alkylate, an isoparaffin fraction, and an alkylate fraction, and
    (f) recycling at least a portion of said normal paraffin fraction in (e) to each point of downstream introduction of olefin in (b) in an amount sufficient to provide a hydrocarbon to olefin volume ratio of about 2 to 1 to about 50 to 1.

2. A process according to claim 1 wherein said olefins include a lighter and a heavier olefin, the heavier olefin is introduced adjacent the upstream end of said zone, and said lighter olefin is introduced at an intermediate section of said zone.

3. A process according to claim 1 wherein said isoparaffin is isobutane and said olefins are butylene and propylene.

4. A process according to claim 3 wherein said butylene is introduced at the inlet end of said zone and said propylene is introduced at an intermediate section of said zone.

5. A process according to claim 1 wherein said olefins include a lighter olefin and a heavier olefin, the lighter olefin is introduced adjacent the upstream end of said zone, and said heavier olefin is introduced at an intermediate section of said zone.

6. A process according to claim 5 wherein said isoparaffin is isobutane, said lighter olefin is propylene, and said heavier olefin is butylene.

7. A process according to claim 1 wherein said normal paraffin fraction recycled is an alkylate-free propane and/or normal butane fraction.

8. A process according to claim 4 wherein the normal paraffin is recycled and introduced along with propylene and said normal paraffin is a propane and/or normal butane fraction freed of alkylate.

9. A process according to claim 1 wherein the olefin introduced in steps (a) and (b) is the same and is selected from single olefins as well as mixtures of olefins.

10. A process according to claim 9 wherein said normal paraffin fraction is recycled to and introduced into the reaction zone at each point of olefin introduction in an amount sufficient to provide a hydrocarbon to olefin volume ratio of about 2 to 1 to about 50 to 1.

11. A process according to claim 9 wherein isoparaffin is also introduced into the reaction zone at the downstream points of olefin addition to the reaction zone.

12. A process according to claim 9 wherein the olefin introduced in steps (a) and (b) is the same and is selected from propylene, butylene, or a mixture of propylene and butylenes and the normal paraffin fraction recycled to the downstream introduction of olefin in (b) is propane.

13. A process according to claim 1 wherein isobutane is alkylated with butylene and with propylene, the reaction zone inlet temperature is in the range of about 50° F. to about 120° F., the reaction zone outlet temperature is in the range of about 80° F. to about 125° F., the isobutane to olefin mole ratio is in the range of about 7:1 to about 40:1, and the HF to total hydrocarbon volume ratio is in the range of about 1:1 to about 10:1.

14. A process according to claim 6 wherein the reaction zone inlet temperature is in the range of about 80° F. to about 125° F. and sufficient pressure to maintain liquid phase conditions, the reaction zone outlet temperature is in the range of about 50° F. to about 120° F., the isobutane to olefin ratio is in the range of about 7 to 1 to about 40 to 1, and the HF to total hydrocarbon volume ratio is in the range of about 1 to 1 to about 10 to 1.

15. A process according to claim 5 wherein said normal paraffin fraction is recycled to and introduced into the reaction zone at each point of olefin introduction in an amount sufficient to provide a hydrocarbon to olefin volume ratio of about 2 to 1 to about 50 to 1.

* * * * *